United States Patent
Massen

(10) Patent No.: US 9,308,069 B2
(45) Date of Patent: Apr. 12, 2016

(54) HERNIA MESH APPARATUS AND METHOD

(75) Inventor: Richard Massen, Taos, NM (US)

(73) Assignee: Richard Massen, Taos, NM (US)

( * ) Notice: Subject to any disclaimer, the term of this patent is extended or adjusted under 35 U.S.C. 154(b) by 241 days.

(21) Appl. No.: 13/702,179

(22) PCT Filed: Dec. 12, 2011

(86) PCT No.: PCT/US2011/064330
§ 371 (c)(1),
(2), (4) Date: Dec. 5, 2012

(87) PCT Pub. No.: WO2012/082581
PCT Pub. Date: Jun. 21, 2012

(65) Prior Publication Data
US 2013/0253545 A1    Sep. 26, 2013

Related U.S. Application Data

(60) Provisional application No. 61/422,411, filed on Dec. 13, 2010.

(51) Int. Cl.
*A61F 2/00* (2006.01)
*A61F 5/24* (2006.01)
*A61L 31/14* (2006.01)

(52) U.S. Cl.
CPC ............. *A61F 2/0063* (2013.01); *A61F 5/24* (2013.01); *A61L 31/14* (2013.01); *A61L 31/145* (2013.01); *A61L 31/146* (2013.01); *A61F 2210/0061* (2013.01); *A61F 2240/002* (2013.01)

(58) Field of Classification Search
CPC .............. A61B 17/00234; A61B 17/0057; A61B 19/5244; A61B 2019/5246; A61B 2019/5248; A61B 2019/5251; A61F 2002/0068; Y10S 623/902
See application file for complete search history.

(56) References Cited

U.S. PATENT DOCUMENTS

| | | | | |
|---|---|---|---|---|
| 5,456,720 A * | 10/1995 | Schultz et al. | ............. | 623/23.64 |
| 5,569,273 A * | 10/1996 | Titone | .................. | A61F 2/0063 442/1 |
| 6,066,776 A * | 5/2000 | Goodwin | ............. | A61F 2/0063 606/151 |
| 6,112,704 A | 9/2000 | Altafi | | |
| 6,180,848 B1 * | 1/2001 | Flament | ............ | A61B 17/0057 606/151 |
| 6,241,768 B1 * | 6/2001 | Agarwal et al. | ........... | 623/11.11 |

(Continued)

OTHER PUBLICATIONS

Bell, R. C. W. et al., "Laparoscopic inguinal hernia repair using an anatomically contoured three dimensional mesh," Surgical Endoscopy (2003) 17(11):1784-1788 (abstract).

*Primary Examiner* — Jocelin Tanner

(57) ABSTRACT

A dual-layer hernia mesh can be configured according to a three-dimensional map of a hernia defect(s) and a hernia volume(s) of a patient. The front portion of the mesh can be configured utilizing, for example, a three dimensional map of hernia sac volumes obtained from a CT scan. The front portion of the mesh exactly fits into the hernia sac. The back portion of the hernia mesh is a sheet of mesh material that overlaps over onto the normal muscles and fascia. A "foam" collapsible mesh and/or a flat mesh with expandable hydrogel deposited in variable thickness according to the hernia defect can be utilized as a dual-layer hernia mesh for repair. The hydrogel mesh when combined with water or saline expands and fits into the hernia defect or defects. Both "foam" and hydrogel meshes adhere to the tissues of the hernia sac and then contracts over time. The hernia sac volume slowly disappears, restoring a more normal contour to the abdominal wall.

15 Claims, 5 Drawing Sheets

(56) References Cited

U.S. PATENT DOCUMENTS

| | | | |
|---|---|---|---|
| 6,652,595 B1* | 11/2003 | Nicolo | A61F 2/0063 600/36 |
| 2001/0027347 A1* | 10/2001 | Rousseau | 623/23.72 |
| 2001/0049539 A1 | 12/2001 | Rehil | |
| 2003/0004581 A1* | 1/2003 | Rousseau | 623/23.74 |
| 2004/0024470 A1* | 2/2004 | Giordano et al. | 623/23.51 |
| 2004/0253185 A1* | 12/2004 | Herweck et al. | 424/10.2 |
| 2005/0021058 A1* | 1/2005 | Negro | 606/151 |
| 2005/0043835 A1* | 2/2005 | Christensen | A61C 13/0004 700/98 |
| 2006/0015143 A1* | 1/2006 | Alvarado | 606/213 |
| 2006/0173472 A1* | 8/2006 | Starkebaum et al. | 606/153 |
| 2007/0032881 A1* | 2/2007 | Browning | A61F 2/0063 623/23.72 |
| 2007/0198040 A1* | 8/2007 | Buevich | A61F 2/0063 606/151 |
| 2010/0087839 A1 | 4/2010 | Nielsen et al. | |
| 2010/0318108 A1* | 12/2010 | Datta | A61L 31/10 606/151 |

\* cited by examiner

HERNIA MESH APPARATUS AND METHOD

TECHNICAL FIELD

Embodiments are generally related to devices utilized in hernia repair procedures. Embodiments also relate to a hernia mesh. Embodiments additionally relate to a dual-layer hernia mesh that can fit into hernia defects and sacs. Embodiments additionally relate to dual-layer hernia mesh devices manufactured according to a three-dimensional map of a hernia defect and the hernia volume of a patient and methods of manufacture thereof.

BACKGROUND OF THE INVENTION

A hernia is a failure of a body barrier to restrain the protrusion of organs from one area into another. Normally, the anterior (front) abdominal wall restrains abdominal contents, including intestine, from protruding through the muscles and fascia to a position under the skin. In ventral hernias, the abdominal wall has separated and intestine or other contents herniate through the weakness to a subcutaneous position on the abdominal wall. The muscular separation is called the hernia defect. As the intestines protrude through the hernia defect, they come to rest in the fatty soft tissue under the skin called subcutaneous fascia. The volume of intestine that protrudes through the muscular or fascial defect is called the hernia volume, or sometimes the hernia sac.

Ventral hernias refer to any hernia through the anterior abdominal wall. They can arise spontaneously. More commonly, ventral hernias arise in an area of a previous surgical incision through the muscles and fascia of the abdominal wall and are called incisional hernias. They arise because even though the skin of an incision has healed, the area where the deeper muscles and fascia were originally sewn together separates over time, allowing the intestines to protrude.

Ventral hernias cause problems because they are painful, unsightly, and represent a threat to the patient. If the herniating intestines get strangled by the constricting hernia defect border, intestinal death can occur. Incisional hernias arise as a long-term complication after abdominal surgeries, in about 10-20% of abdominal surgery patients. It is estimated that one hundred thousand hernia meshes are placed annually in the United States for ventral hernia repairs.

All ventral hernias, except for small spontaneous (umbilical or epigastric) hernias, require mesh for repair. Umbilical and epigastric hernias also require mesh repair when they are larger than 2 cm diameter. The mesh is made of some type of strong synthetic, or biologic, fabric-like material.

Ventral hernias can be repaired by open or laparoscopic techniques. In open technique, an incision is re-made directly through the original incision that caused the hernia. The hernia sac is dissected from the surrounding subcutaneous fascia and the fascial edges of the hernia defect are defined. The surgeon places a mesh into the abdomen, through the opened hernia defect. A flat mesh is chosen so that its area overlaps the edges of the defect from behind, for a few centimeters in all directions from the defect edges. It is sewn in place behind the defect and usually inside the abdomen.

In a laparoscopic repair, an incision going through the prior skin incision site is avoided. Fiberoptic cameras and small plastic ports are used to perform surgery inside the abdomen. The ports are placed through small incisions, away from the original surgery site. The abdomen is inflated like a tent and a camera is used to see inside the abdomen. In laparoscopy, the view towards the "ceiling" shows the posterior aspect of the anterior abdominal wall. Any bowel herniating into the defect at the time of surgery is removed, exposing the hernia defect and sac. The defect size is approximated and a suitable-size mesh is chosen to be placed in the abdomen. Like in open hernia repairs, the mesh must overlap the defect edges by a few centimeters in all directions. It is sewn or tacked in place against the posterior aspect of the anterior abdominal wall.

After open or laparoscopic ventral hernia surgery, the hernias still recur in 10-30% of cases. Such surgeries fail because the mesh fails to keep the bowel out of the hernia defect. Sometimes the mesh does not overlap the defect widely enough when sewn in place. Sometimes gaps form between the stitches or tacks holding the mesh in place and the bowel works itself between the gaps. Sometimes the mesh twists, kinks, or retracts in some way, permitting bowel access to the defect. The high failure rate is considered a major surgical problem in hernia surgery.

Irregular or multiple defect areas and irregular hernia sac volumes contribute to recurrence after repair. A large incisional hernia often consists of a dominant, more obvious defect, accompanied by smaller defects, not initially appreciated before surgery. These smaller defects are well known to surgeons and the problem is often referred to as a "Swiss Cheese" defect because of the multiple holes. The multiple volumes and areas often require open-style surgery to use larger incisions and meshes than initially expected, with increased associated morbidity from the large incision. The multiple volumes and defects also make placement of the hernia mesh difficult to gauge laparoscopically, where appropriately-sized meshes and their placements are selected on the basis of indirect visualization techniques.

In both open and laparoscopic procedures, significant time is spent measuring and estimating defect size, and then fixing the mesh in place using through-and-through sutures to the normal abdominal wall muscles at the edge of the hernia defects. Since the hernia defect area is covered from behind by conventional laparoscopic ventral hernia meshes, but the hernia sac volume isn't "filled," the sac volume always fills with blood or serum (forming a hematoma, or seroma, respectively). In open repair, the problem can be avoided by placing suction drains between the skin and the mesh to drain and collapse hernia sac space. The drains are unsightly, uncomfortable, and importantly may contribute to mesh infection, a difficult complication. Drains are not placed in a laparoscopic repair, but seromas and hematomas are unavoidable. Therefore, there exists a need for a new hernia mesh that can exactly and easily fit into hernia sac and collapse the hernia sac space permanently.

BRIEF SUMMARY

The following summary is provided to facilitate an understanding of some of the innovative features unique to the disclosed embodiment and is not intended to be a full description. A full appreciation of the various aspects of the embodiments disclosed herein can be gained by taking the entire specification, claims, drawings, and abstract as a whole.

It is, therefore, one aspect of the disclosed embodiments to provide for a hernia mesh.

It is another aspect of the disclosed embodiments to provide for a dual-layer hernia mesh that can fit into hernia defects and sacs.

It is a further aspect of the present invention to provide for a dual-layer hernia mesh manufactured according to three dimensional map of a hernia defect and hernia volume of a patient and methods of its manufacture.

The aforementioned aspects and other objectives and advantages can now be achieved as described herein. A 3-D map of a hernia defect and hernia volume can be obtained from an imaging technique (e.g., MRI, Computed Tomography (CT) scan, terahertz radiation scanning or other 3D imaging technology). The data can be utilized to custom manufacture each mesh with an anterior or front "volume" that fits exactly into the hernia sac. The back or posterior of the customized mesh, like any other ventral hernia mesh, is a sheet of mesh material that overlaps over onto the normal muscles and fascia. The mesh can be easily placed laparoscopically, taking advantage of the exact fit of the mesh's front into the hernia defect. It would be expected to have little chance of migrating, gapping, or buckling since the volume of the hernia sac is now filled by the front part of the mesh. Since the front part of the mesh fills all or part of the hernia sac, it would retard bowel from moving back into the hernia sac volume.

A "foam" compressible front mesh and/or a flat front mesh with expandable hydrogel deposited in variable thickness according to the hernia defect can be utilized as part of a mesh for hernia repair. The hydrogel mesh when combined with water or saline expands and fits into the hernia defect or defects. Both "foam" and hydrogel meshes adhere to the tissues of the hernia sac and then may contract over time. The hernia sac volume slowly disappears and restores a more normal contour to the abdominal wall.

BRIEF DESCRIPTION OF THE DRAWINGS

The accompanying figures, in which like reference numerals refer to identical or functionally-similar elements throughout the separate views and which are incorporated in and form a part of the specification, further illustrate the disclosed embodiments and, together with the detailed description of the invention, serve to explain the principles of the disclosed embodiments.

DETAILED DESCRIPTION

The particular values and configurations discussed in these non-limiting examples can be varied and are cited merely to illustrate at least one embodiment and are not intended to limit the scope thereof. Note that for an explanatory purpose, ventral hernia is discussed. The invention can also be utilized in any other hernia involving a surgically accessible hernia sac that could be considered including inguinal hernias. Repairs in hiatal hernias (hernias through the diaphragm), congenital or traumatic diaphragmatic hernias, and other less common type of abdominal and pelvic hernias (obturator or flank hernias, for example) are also possible with the invention. Repairs of other soft tissue abnormalities are also possible.

Figure 1A:
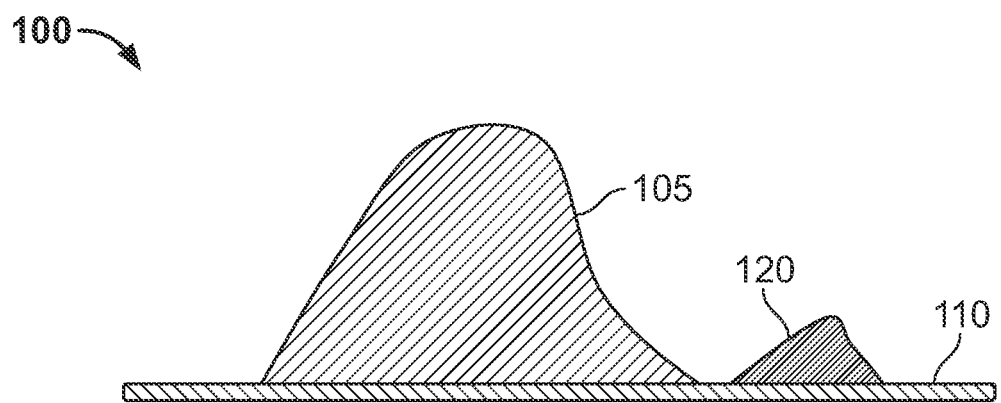
FIGS. 1A and 1B illustrate a side view and a perspective view of a hernia mesh respectively, in accordance with the disclosed embodiments.
Figure 1B:
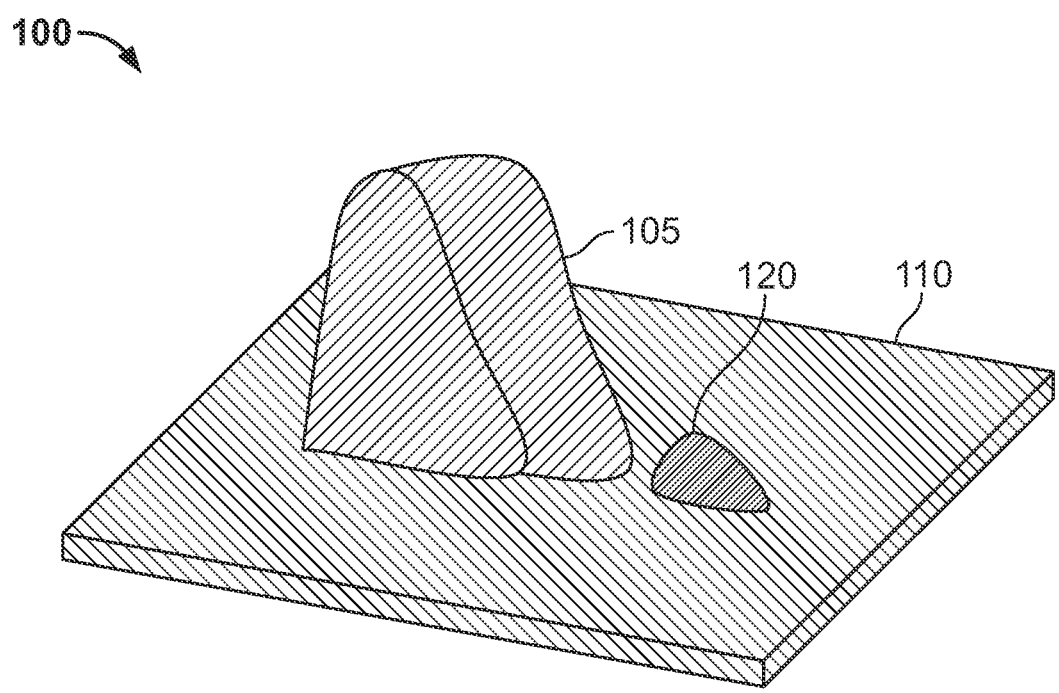

FIG. 1A and FIG. 1B illustrates a side view and a perspective view of a hernia mesh 100 respectively, in accordance with the disclosed embodiments. The mesh 100 comprises of a front portion 105 and back portion 110. Note that the front portion and back portion of the mesh are defined according to the placement of mesh in the defected area and not as per the views of FIG. 1A and FIG. 1B. The front portion of the mesh is custom manufactured according to the hernia sac (not shown) of a patient. Multiple defects can be filled with foam or gel to fill smaller defects 120.

Figure 2:
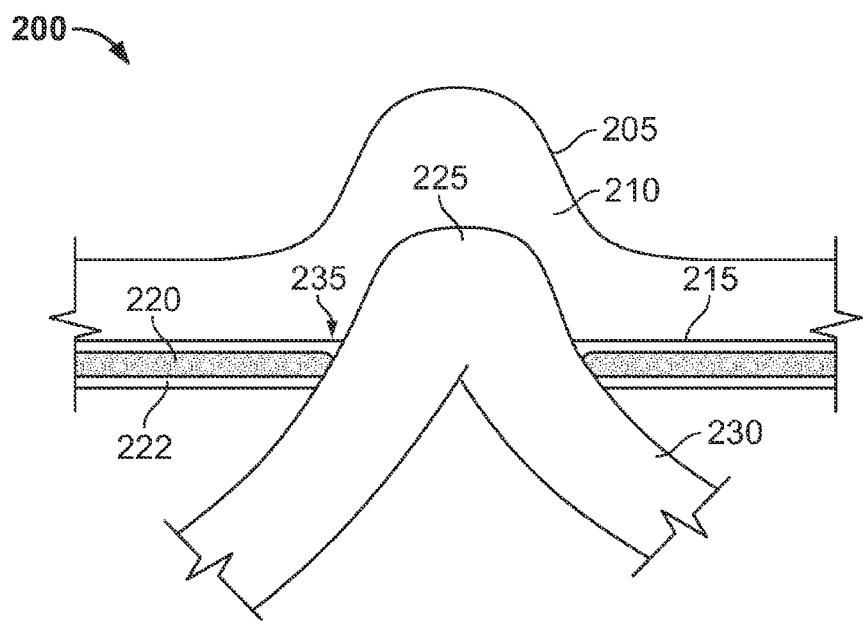
FIG. 2 illustrates a perspective view of hernia before repair, in accordance with the disclosed embodiments.

FIG. 2 illustrates a perspective view of hernia 200 before repair, in accordance with the disclosed embodiments. The abdominal wall 215 weakens and allows the intestine 230 to protrude outside and form a hernia sac 225. The muscular separation is called the hernia defect 235. It arises from a separation of the abdominal wall muscles 220 and their dense surrounding connective tissue, called abdominal wall fascia 222. As the intestines 230 protrude through the hernia defect 235, they come to rest in the fatty soft tissue under the skin 205, called subcutaneous fascia 210. The volume of intestine 230 that protrudes through the fascia defect 235 is called the hernia sac 225.

Figure 3:
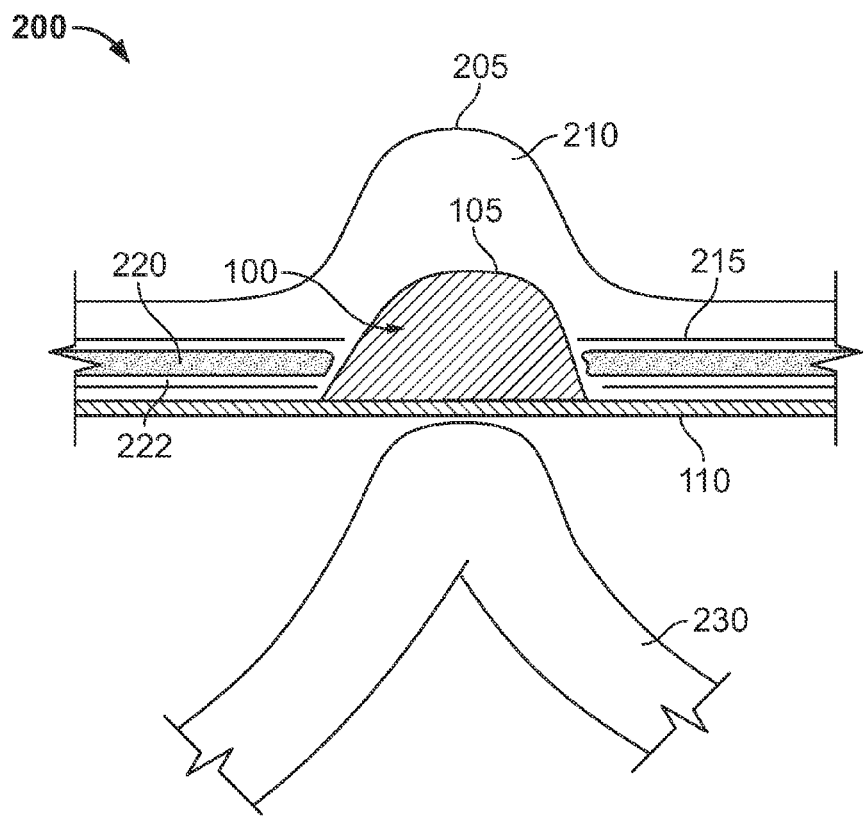
FIG. 3 illustrates a perspective view of hernia after placing a mesh, in accordance with the disclosed embodiments.

FIG. 3 illustrates a perspective view of hernia 200 after placing a mesh 100, in accordance with the disclosed embodiments. A Computed Tomography (CT) scan can be utilized for obtaining a three dimensional map of hernia sacs 225 and hernia volumes. The data can be utilized to custom manufacture the mesh 100 with a front portion 105 that fits exactly into the hernia sac 225. Multiple projections of the mesh 100 can fill into multiple other volumes, not shown. The back portion 110 of the customized mesh 100, like any other hernia mesh, is a sheet of strong synthetic, or biologic, fabric-like material that overlaps over onto the normal muscles 220 and fascia 222. The mesh 100 can be easily placed laparoscopically, taking advantage of the exact fit of the front portions 105 and 120 into the hernia defects 235. It would be expected to have little chance of migrating, gapping, or buckling since the volume of the hernia sac 225 is now filled by the front part of the mesh. Since the front potion 105 of the mesh 100 fills all or part of the hernia sac 225, it would retard bowel from moving back into the hernia sac volume since the volume is already occupied by the front portion 105 of the artificial mesh 100. Note that mesh, artificial mesh, custom mesh, and customized mesh are used interchangeably throughout the specification and all refers the same reference numeral 100.

Figure 4:
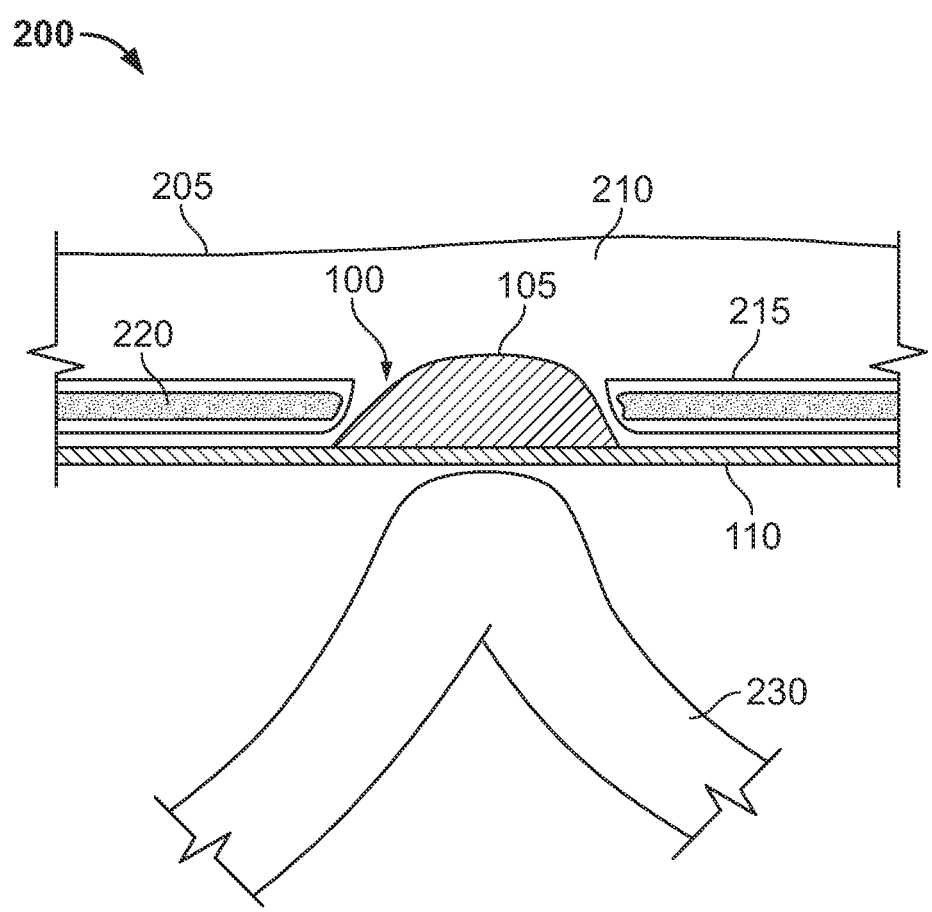
FIG. 4 illustrates a perspective view of hernia after repair, in accordance with the disclosed embodiments.

FIG. 4 illustrates a perspective view of hernia 200 after repair, in accordance with the disclosed embodiments. The front portion 105 of the mesh 100 is made of either "foam" or hydrogel. Ideally, the "foam" or hydrogel adheres to the tissues of the hernia sac 225 and then contracts over time. Over this time, the volume of hernia sac 225 gets drawn in gradually towards the back portion 110 of the mesh 100. Thus, the volume of hernia sac 225 slowly disappears, restoring a more normal contour to the abdominal wall 210.

Figure 5:
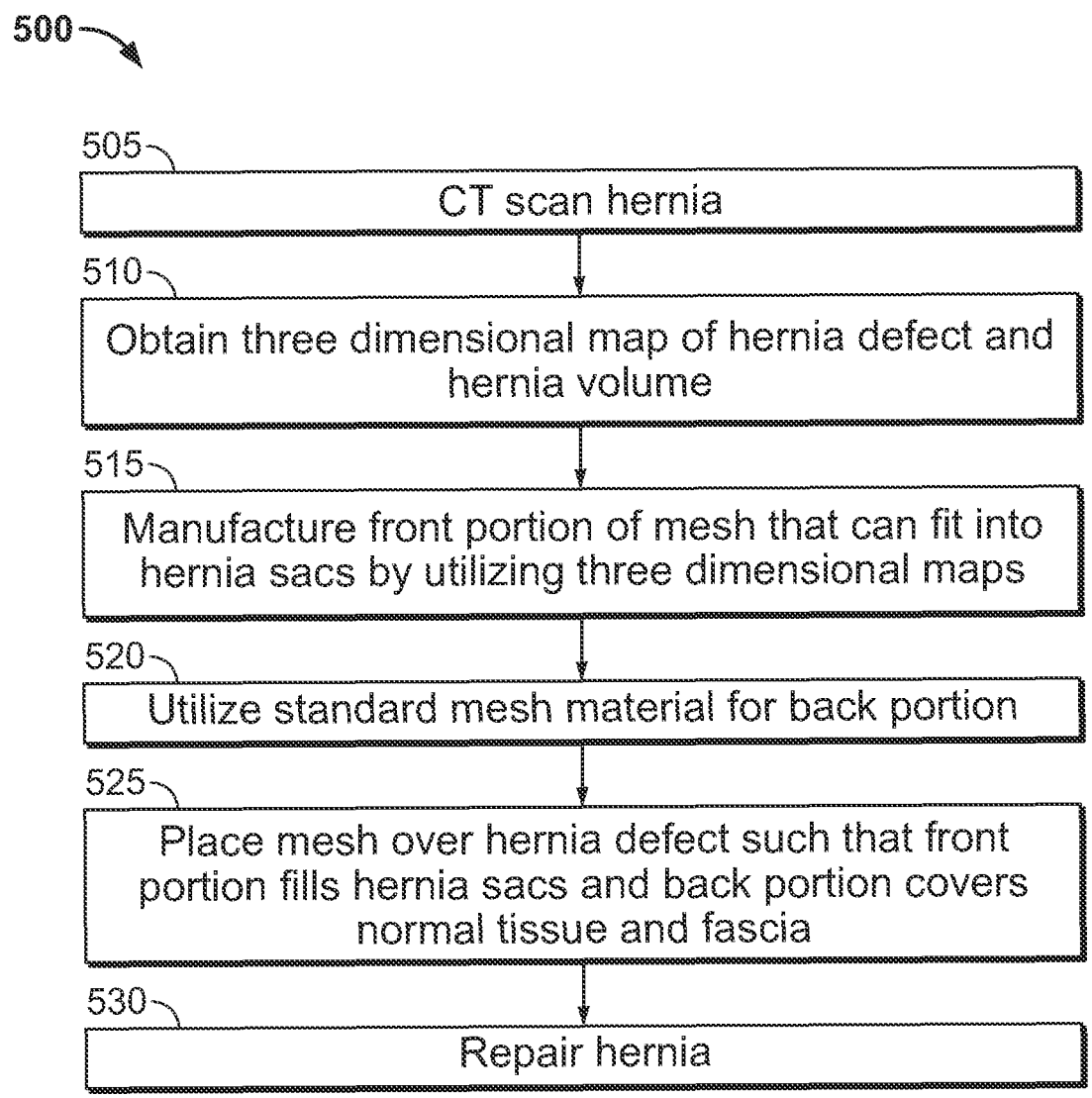
FIG. 5 illustrates a flow chart of logical operations depicting a method of repairing a hernia.

FIG. 5 illustrates a flow chart of logical operations depicting a method 500 of a process for repairing a hernia, in accordance with the disclosed embodiments. Initially, CT scan of a hernia is taken, as indicated at block 505. Then, as illustrated at block 510, a three dimensional map of a hernia defect and hernia volume are obtained from the CT scan. The front portion of the mesh is manufactured according to the hernia defect and hernia volume of the patient, as depicted at block 515. As described at block 520, a standard mesh material made of strong synthetic, or biologic, fabric-like material can be utilized for the back portion of the mesh. As depicted at block 525, the mesh can be placed into the hernia defect such that the front portion fills the hernia sac and the back portion covers normal tissue and fascia. Finally, the mesh adheres to the tissues of hernia sac and repairs the hernia, as depicted at block 530.

The functionality of the invention is further described in the following non-restrictive examples.

Example 1

The hernia mesh can be configured from "foam". The mesh can be pressed down small enough to allow the mesh to be rolled up and deployed through a small laparoscopic port. Then the mesh is unrolled inside the inflated abdomen and fitted into the exposed hernia sac spaces. The foam described herein can be biocompatible, expansile over time, and bacteria resistant.

Example 2

The hernia mesh disclosed herein can be configured from an expandable hydrogel, relatively flat when machined, but rapidly expanded when exposed to saline or water. The hydrogel is deposited on the mesh during manufacture in different thicknesses over the hernia defect areas. Once in the abdomen, the mesh is combined with water or saline, and the hydrogel expands, fitting into the hernia defect or defects. Hydrogel mesh is biocompatible, expansile over time, and bacteria resistant.

Figure 6A:
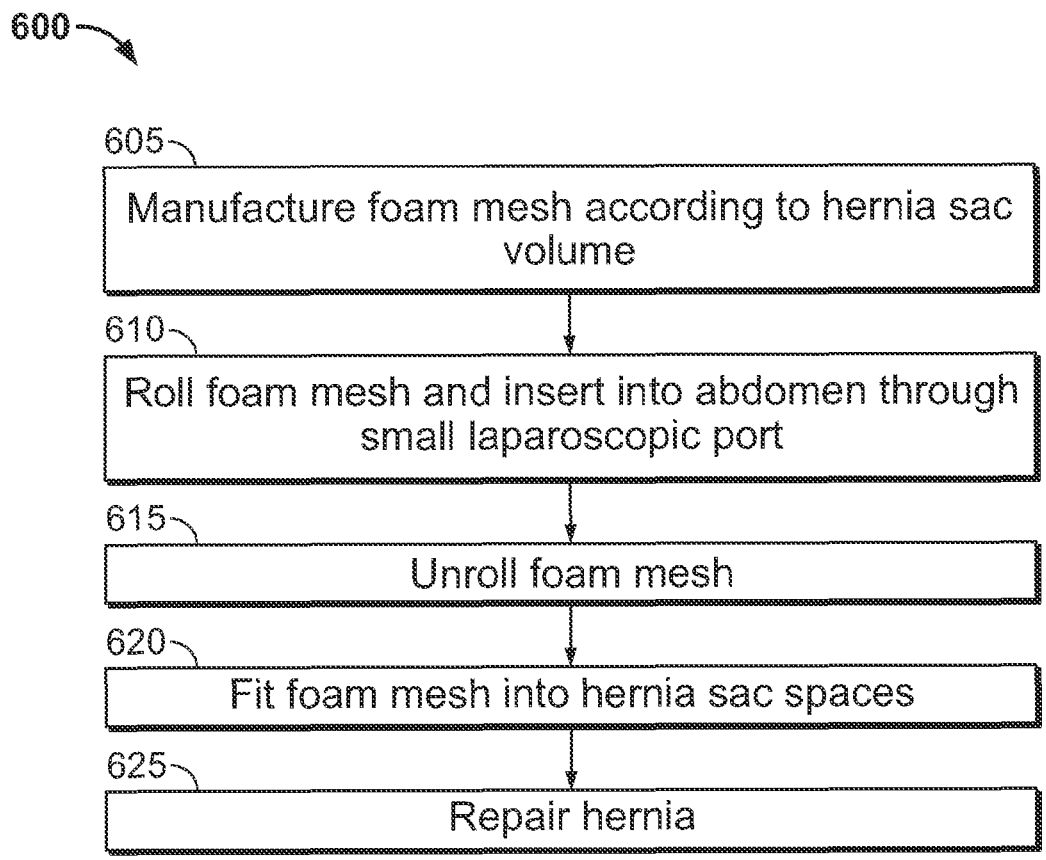
FIG. 6A illustrates a flow chart of logical operations depicting a method of repairing a hernia by utilizing, for example, a "foam" mesh, in accordance with the disclosed embodiments.

FIG. 6A illustrates a flow chart of logical operations depicting a method 600 of repairing a hernia defect by utilizing "foam" mesh, in accordance with the disclosed embodiments. As illustrated at block 605, the front portion of the mesh made of "foam" can be manufactured according to the hernia sac volumes of a patient. The hernia sac volume information can be obtained from a three dimensional map of CT scan. The mesh can be pressed, rolled, and inserted into the abdomen through a small laparoscopic port, as described at block 610. Then, the mesh can be unrolled inside the abdomen and then exactly fitted into the hernia defect, as depicted at block 615 and block 620, respectively. The mesh adheres to the tissues of hernia sacs and then contracts over time. Over time, the subcutaneous hernia sac volumes are drawn in gradually towards the back portion of the mesh. Thus, finally as illustrated at block 625, the hernia sac volumes slowly disappear, restoring a more normal contour to the abdominal wall.

Figure 6B:
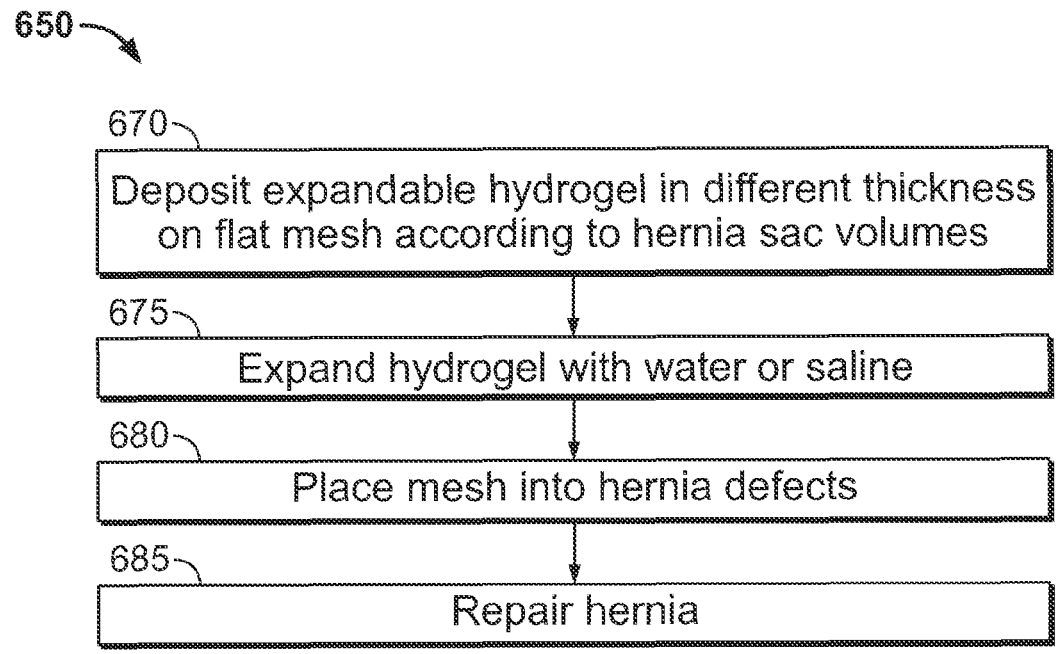
FIG. 6B illustrates a flow chart of logical operations depicting a method of repairing a hernia by utilizing, for example, a hydrogel mesh, in accordance with the disclosed embodiments.

FIG. 6B illustrates a flow chart of logical operations depicting a method 650 of repairing a hernia defect by utilizing a hydrogel mesh, in accordance with the disclosed embodiments. As illustrated at block 670, the front portion of the mesh can be configured as a flat mesh by depositing hydrogel in varying thicknesses according to the hernia defects. Then, the mesh can be combined with water or saline, for example, as indicated at block 675. The hydrogel deposited on the mesh can expand when combined with water or saline, and the mesh exactly fits into the hernia sacs as illustrated at block 675. The mesh can be placed into the hernia defect areas as described at block 680. The mesh adheres to the tissues of hernia sac and then contracts over time. Over time, the subcutaneous hernia sac volume gets drawn in gradually towards the back portion of the mesh. Finally, as illustrated at block 685, the hernia sac volume slowly disappears, restoring a more normal contour to the abdominal wall.

Since the front part of the dual-layer mesh fits exactly into the hernia defects and volumes, it would be easy to place. A minimal amount of time is spent getting the mesh to fit over and into the hernia. Through-and-through sutures of the mesh to the abdominal wall could probably be avoided, shortening operating time, and increasing postoperative comfort, since the full-thickness sutures are painful. Also, recurrence of mesh failure would be avoided. Since incisions through the original incision is avoided, less pain and infection would be expected.

Based on the foregoing, it can be appreciated that a number of different embodiments, preferred and alternative, are disclosed herein. For example, in one embodiment, a hernia mesh apparatus can include a front portion that fits precisely into hernia sacs, wherein the front portion is configured according to a three-dimensional map of hernia defects and hernia volumes, and a back portion that covers normal muscles and fascia. In another embodiment, the three-dimensional map of hernia defects and hernia volumes can be obtained utilizing a three-dimensional imaging technology such as, for example, a terahertz radiation imaging technology, a MRI, a Computed Tomography Scanner, etc. In another embodiment, the aformentioned front portion can comprise a compressible foam. In yet another embodiment, the aforementioned front portion can comprise an expandable hydrogel material. In still another embodiment, the expandable hydrogel material can be deposited in a variable thickness according to the hernia defects and the hernia volumes.

In other embodiments, the expandable hydrogel material can expand rapidly on exposure to saline. In yet other embodiments, the expandable hydrogel material can rapidly expand on exposure to water. In still other embodiments, the front portion can adhere to tissues of the hernia sac and then contract over time. In other embodiments, the front portion can comprise a material that is biocompatible and bacteria resistant. In still another embodiment, the front portion can comprise a material that is biocompatible. In yet other embodiments, the front portion can comprise a material that is bacteria resistant.

In another embodiment, a hernia mesh apparatus can be configured, which includes a front portion that fits precisely into hernia sacs, wherein the front portion is configured according to a three-dimensional map of hernia defects and hernia volumes, the front portion comprising at least one of a compressible foam or an expandable hydrogel material; and a back portion that covers normal muscles and fascia. In other embodiments, the expandable hydrogel material can be deposited in a variable thickness according to the hernia defects and the hernia volumes. In other embodiments, the expandable hydrogel material can rapidly expand on exposure to saline or water. In still other embodiments, the front portion can adhere to tissues of the hernia sacs and then contracts over time. In yet other embodiments, the front portion can comprise a material that is biocompatible and/or bacteria resistant.

In another embodiment, a hernia mesh method can be provided, which includes configuring a front portion according to a three-dimensional map of hernia defects and hernia volumes; fitting the front portion precisely into hernia sacs; and providing a back portion that covers normal muscles and fascia. In other embodiments, an operation can be implemented for obtaining the three-dimensional map of hernia defects and hernia volumes utilizing a 3D scanning technology. In still other embodiments, a step can be provided for configuring the front portion from at least one of a compressible foam or an expandable hydrogel material. In yet other embodiments, a step can be provided for configuring the front portion to comprise a material that is biocompatible and bacteria resistant.

It will be appreciated that variations of the above disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

What is claimed is:

1. An insert for laparoscopic hernia repair, comprising:
a front portion formed of a material having a smaller insertion position and a larger placement position, the front portion conforming to a pre-determined shape of a hernia sac, the front portion configured to fit precisely into the hernia sac to fill a space within the sac to prevent bowel from moving back into the hernia sac, wherein said front portion is preformed to conform to the pre-determined shape by a three-dimensional map of a hernia defect and hernia volume, the front portion having an irregular shape, wherein first, second and third transverse planes through the front portion between an upper portion and a lower portion have different shapes and dimensions;
a back portion that covers normal muscles and fascia, the front portion extending from the back portion into the hernia sac; and
a second projection spaced from the front portion and extending from the back portion, the second projection being irregular in configuration and configured to fill a volume.

2. The apparatus of claim 1 wherein said three-dimensional map of hernia defect and hernia volume is obtained utilizing a three-dimensional imaging technology.

3. The apparatus of claim 1 wherein said front portion comprises a compressible foam.

4. The apparatus of claim 1 wherein said the front portion is configured to adhere to tissues of said hernia sac and then contracts over time.

5. The apparatus of claim 1, wherein said front portion comprises a material that is biocompatible and bacteria resistant.

6. The apparatus of claim 1, wherein said front portion comprises a material that is bacteria resistant.

7. An insert for laparoscopic hernia repair, comprising:
a front portion formed of a material having a smaller insertion position and a larger placement position, the front portion conforming to a pre-determined shape of a hernia sac, the front portion configured to fit precisely into the hernia sac to fill a space within the sac to prevent bowel from moving back into the hernia sac, wherein said front portion is preformed to conform to the pre-determined shape by a three-dimensional map of a hernia defect and hernia volume, the front portion having an irregular shape, wherein first, second and third transverse planes through the front portion between an upper portion and a lower portion have different shapes and dimensions; and
a back portion that covers normal muscles and fascia, the front portion extending from the back portion into the hernia sac;
wherein the front portion comprises an expandable hydrogel material, the expandable hydrogel material is deposited in a variable thickness according to said hernia defect and said hernia volume.

8. The apparatus of claim 7 wherein said expandable hydrogel material rapidly expands on exposure to one or both of saline or water.

9. A method of laparoscopic hernia repair to fill the volume of a hernia sac and block a bowel from entering the hernia sac, the method comprising
configuring a front portion of a hernia repair insert to conform to a three-dimensional map of a hernia defect and a hernia volume within the hernia sac, the front portion having an irregular configuration;
laparoscopically inserting the front portion in a smaller profile configuration;
fitting said front portion precisely into the hernia sac, the front portion due to its preformed irregular configuration from the three dimensional map conforming to a size and shape of the hernia sac to fill the volume of the hernia sac and block bowel from re-entering the hernia sac; and
attaching a back portion that covers normal muscles and fascia;
wherein the front portion collapses the hernia sac permanently.

10. The method of claim 9 further comprising obtaining said three-dimensional map of the hernia defect and hernia volume utilizing a Computed Tomography Scanner.

11. The method of claim 9 further comprising configuring said front portion from at least one of a compressible foam or an expandable hydrogel material.

12. The method of claim 9 further comprising the step of compressing the hernia repair insert to obtain the smaller profile configuration.

13. The method of claim 9, wherein the back portion is placed due to the precise fitting of the front portion in the hernia sac.

14. The method of claim 9, wherein the back portion can be attached without through and through sutures through an abdomen.

15. The method of claim 9, wherein first, second and third transverse planes through the front portion between an upper portion and a lower portion have different shapes and dimensions.

* * * * *